US011426072B2

(12) United States Patent
Amma et al.

(10) Patent No.: US 11,426,072 B2
(45) Date of Patent: Aug. 30, 2022

(54) OPHTHALMIC SCANNING SYSTEM AND METHOD

(71) Applicant: Optos Plc, Scotland (GB)

(72) Inventors: Sriram Vikraman Sithalakshmi Amma, Dunfermline (GB); Praveen Ashok, Dunfermline (GB); Daniel Hurst, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 293 days.

(21) Appl. No.: 16/594,985

(22) Filed: Oct. 7, 2019

(65) Prior Publication Data

US 2021/0100450 A1 Apr. 8, 2021

(51) Int. Cl.
*A61B 3/18* (2006.01)
*A61B 3/00* (2006.01)
*A61B 3/10* (2006.01)
*A61B 3/12* (2006.01)

(52) U.S. Cl.
CPC .............. *A61B 3/18* (2013.01); *A61B 3/0025* (2013.01); *A61B 3/102* (2013.01); *A61B 3/12* (2013.01)

(58) Field of Classification Search
CPC ......... A61B 3/18; A61B 3/0025; A61B 3/102; A61B 3/12; A61B 3/1025; A61B 3/10; A61B 3/1225; A61B 5/0073; A61B 5/0059
USPC ....................................................... 351/206
See application file for complete search history.

(56) References Cited

U.S. PATENT DOCUMENTS

| 9,740,003 | B2* | 8/2017 | Potsaid | A61B 3/102 |
| 2007/0195269 | A1* | 8/2007 | Wei | G06T 7/11 351/221 |
| 2012/0033227 | A1* | 2/2012 | Bower | A61B 3/102 356/479 |
| 2014/0028997 | A1* | 1/2014 | Cable | G01B 9/02091 356/51 |
| 2015/0109579 | A1 | 4/2015 | Orlowski et al. | |
| 2015/0216408 | A1* | 8/2015 | Brown | A61B 3/1025 351/206 |
| 2021/0093187 | A1 | 4/2021 | Ito | |
| 2021/0275010 | A1 | 9/2021 | Muyo et al. | |

FOREIGN PATENT DOCUMENTS

| JP | 59-97118 | 7/1984 |
| JP | 2015-80726 | 4/2015 |
| JP | 2018-61622 | 4/2018 |

(Continued)

OTHER PUBLICATIONS

European Search Report dated Feb. 21, 2015 in European Application No. 20197404.5-1126.

(Continued)

*Primary Examiner* — Mohammed A Hasan

(57) ABSTRACT

An ophthalmic scanning system includes a first imaging modality, a second imaging modality different from the first imaging modality, and a control system that maps the first imaging modality to the second imaging modality by compensating for at least one of an optical-mechanical and an electro-mechanical projection difference between the first and second imaging modalities. The control system provides a scan location for the second imaging modality based on a scan location of the first imaging modality.

20 Claims, 14 Drawing Sheets

(56) References Cited

FOREIGN PATENT DOCUMENTS

| JP | 2021053198 A | 4/2021 |
|---|---|---|
| WO | 2019034228 A1 | 2/2019 |
| WO | 2019034230 A1 | 2/2019 |
| WO | 2019-189223 | 3/2019 |

OTHER PUBLICATIONS

Notice of Reasons for Refusal (dated Sep. 30, 2021 and) issued in Japanese Patent Application 2020-170040 (2 sheets); English translation attached (3 sheets).

* cited by examiner

OPHTHALMIC SCANNING SYSTEM AND METHOD

TECHNICAL FIELD

Example aspects herein relate generally to ophthalmic scanning systems and methods, and, more particularly, to ophthalmic scanning systems and methods that provide co-alignment, target tracking, and non-linearity compensation.

BACKGROUND

Ophthalmoscopes can include multiple scanning modalities in the same instrument. For example, ophthalmoscopes can include both a scanning laser ophthalmoscope (SLO) modality and an optical coherence tomography (OCT) modality to capture two-dimensional and three-dimensional images of the retina of the eye. The SLO and OCT modalities use separate laser light beams that are directed toward the retina of the eye for capturing images thereof.

Scan repeatability and location accuracy depend on the alignment of the light beams. Thus, alignment of the light beams at the retina can be helpful to ensure that the scanning modalities capture the same data from the same location. Any differences in the alignment of the light beams between the different scanning modalities can result in scan location errors, scan sizing errors, and/or scan linearity errors, resulting in image/feature correlation errors.

In various ophthalmic scanning configurations, there are multiple factors that affect the alignment of the light beams used by the different scanning modalities. Therefore, it would be useful to correct the alignment of the light beams from the different scanning modalities within an ophthalmoscope to reduce errors between the different scanning modalities.

SUMMARY

In one example aspect herein, an ophthalmic scanning system includes a first imaging modality, a second imaging modality different from the first imaging modality, and a control system that maps the first imaging modality to the second imaging modality by compensating for at least one of an optical-mechanical and an electro-mechanical projection difference between the first and second imaging modalities. The control system provides a scan location for the second imaging modality based on a scan location of the first imaging modality.

In another aspect, a method of mapping first and second imaging modalities comprises: receiving a scan location for the first imaging modality; and providing a scan location for the second imaging modality based on the scan location of the first imaging modality by compensating for at least one of an optical-mechanical and an electro-mechanical projection difference between the first and second imaging modalities.

These and other aspects and embodiments are described in detail below, in relation to the attached drawing figures.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
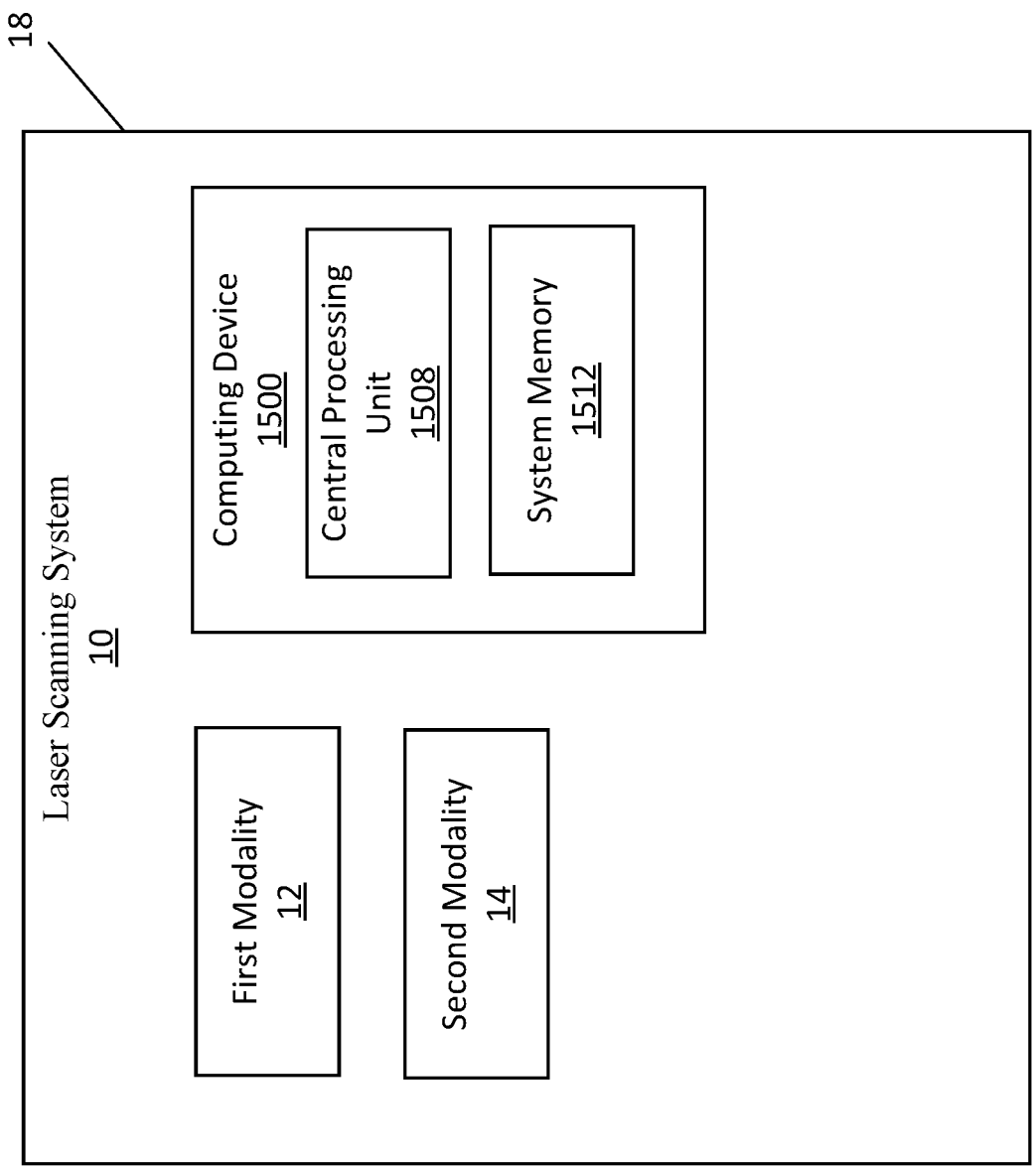
FIG. 1 is a block diagram schematically illustrating an ophthalmic scanning system.

FIG. 1 is schematic diagram illustrating an example ophthalmic scanning system 10. The ophthalmic scanning system 10 includes a first imaging modality 12, a second imaging modality 14, and a computing device 1500. The components of the ophthalmic scanning system 10 including the first imaging modality 12, second imaging modality 14, and computing device 1500 are housed inside of a housing 18 of a single instrument such as an ophthalmoscope, according to one example.

The computing device 1500 operates to control the first and second imaging modalities 12, 14 and has at least one central processing unit 1508 and a system memory 1512 that stores instructions that, when executed by the at least one central processing unit 1508, causes the central processing unit 1508 to perform one or more methods and functions described herein. The computing device 1500 will be described in more detail below in a description of FIG. 15.

In some examples, the first imaging modality 12 is a scanning laser ophthalmoscope (SLO) imaging modality that uses confocal laser scanning microscopy for diagnostic two-dimensional imaging of the retina of the eye. The first imaging modality 12 uses a laser light beam to scan across the retina in a raster pattern to illuminate successive elements of the retina, point-by-point. The light reflected from each retinal point is captured by a photomultiplier. The output of the photomultiplier is recorded and displayed in a digital format. In this manner, the first imaging modality 12 is able to produce high-contrast, detailed images of the retina.

In some examples, the second imaging modality 14 is an optical coherence tomography (OCT) imaging modality that is noninvasive and uses light waves to obtain high resolution cross-sectional images of the retina. The cross-sectional images are generated by analyzing a time delay and magnitude change of low coherence light as it is backscattered by ocular tissues. Layers within the retina can be differentiated and retinal thickness can be measured to aid in the early detection and diagnosis of retinal diseases and conditions including, by example, glaucoma, age-related macular degeneration (AMD), and diabetic eye disease.

In some examples, images are captured sequentially by the first imaging modality 12 and the second imaging modality 14 such that a first image is captured by the first imaging modality 12, and thereafter the first image is used a reference for capturing a second image by the second imaging modality 14.

Figure 2:
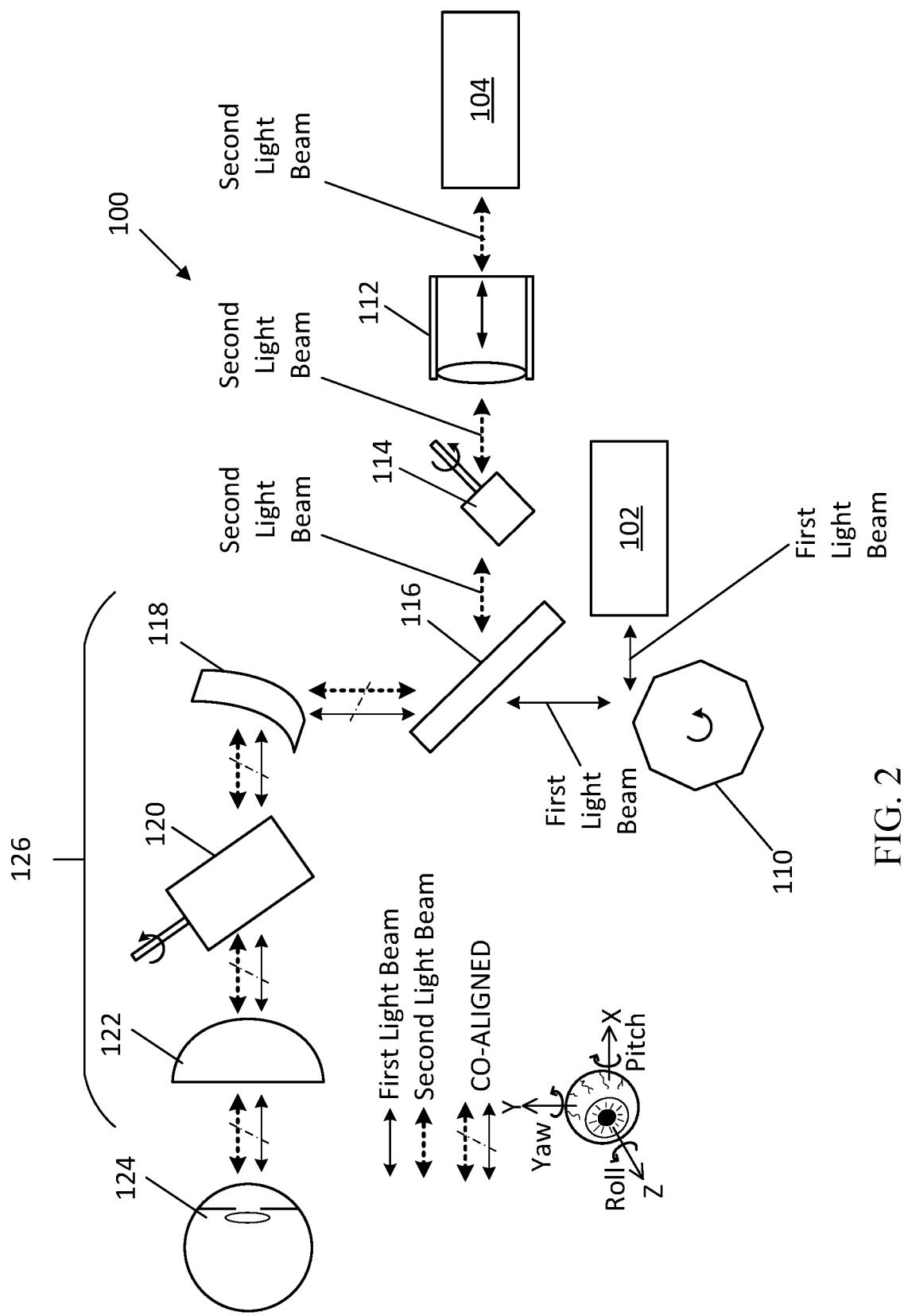
FIG. 2 schematically illustrates scanning and reflecting elements of an ophthalmic scanning system that includes first and second light beam imagers.

FIG. 2 is a schematic view of scanning and reflecting elements of an ophthalmic scanning system 100, according to an example embodiment herein. The ophthalmic scanning system 100 includes a first light beam imager 102 and a second light beam imager 104. In some examples, the first light beam imager 102 is a fundus, SLO, or line imager. In some further examples, the second light beam imager 104 is an OCT or SLO imager.

The ophthalmic scanning system 100 is illustrated in a configuration where light beams from the first and second light beam imagers 102, 104 share a common axis (e.g., x-axis) when directed to the patient eye 124. In other configurations, the first and second light beams (and components described herein (e.g., galvanometer)) do not share a common axis, and instead can be independent in both the x-axis and y-axis, such as, by example, in cases where separate x- and y-scanners are employed.

The first light beam imager 102 directs light beams of a first type (hereinafter "first light beams") to a rotating polygon mirror 110. The rotating polygon mirror 110 scans the first light beams in at least one direction toward an optical beam combiner/splitter 116. Also, the rotating polygon mirror 110 directs reflected first light beams received from the optical beam combiner/splitter 116 back toward the first light beam imager 102. In some examples, the first light beams are SLO light beams.

The second light beam imager 104 directs light beams of a second type (hereinafter "second light beams") to a focus mechanism 112, which directs the second light beams to a galvanometer 114. The galvanometer 114 scans the second light beams in at least one direction toward the optical beam combiner/splitter 116. The galvanometer 114 also directs reflected second light beams received from the optical beam combiner/splitter 116, back toward the second light beam imager 104 by way of focus mechanism 112. In some examples, the second light beams are OCT light beams.

The optical beam combiner/splitter 116 combines the first and second light beams received from the rotating polygon mirror 110 and the galvanometer 114, respectively, to follow a common path 126 towards a target area such as a patient eye 124. The common path 126 includes scanning and reflecting elements such as a slit mirror 118, a secondary galvanometer scanner 120, and a main mirror 122. The main mirror 122 directs the first and second light beams to the patient eye 124. In some examples, the secondary galvanometer scanner 120 (or equivalent) is not a part of the common path 126. Further, the ophthalmic scanning system 100 illustrated in FIG. 2 is just one example of a configuration that can be used with the embodiments described herein, and that additional configurations are contemplated.

The optical beam combiner/splitter 116 also splits the first and second light beams that are reflected back from the patient eye 124 and directs the reflected first and second light beams back to the first and second light beam imagers 102, 104, respectively, for image processing and analysis after the first and second light beams pass back through the common path 126 of scanning and reflecting elements. In some examples herein, the optical beam combiner/splitter 116 is a dichroic mirror.

In the example system illustrated in FIG. 2, the rotating polygon mirror 110 and the galvanometer 114 scan the first and second light beams through the common path 126 and toward the patient eye 124 in a scan pattern that shares at least one common axis (although as described above, in other embodiments the beams are scanned through different axes). As an example, the rotating polygon mirror 110 scans the first light beam to have a vertical pattern in a scan location such as the patient eye 124, and the galvanometer 114 scans the second light beam in the same vertical pattern such that the first and second light beams share a common horizontal axis (i.e., x-axis). As another example, the rotating polygon mirror 110 can scan the first light beam to have a horizontal pattern in a scan location such as the patient eye 124, and the galvanometer 114 can scan the second light beam in the same horizontal pattern such that the first and second light beams share a common vertical axis (i.e., y-axis). It is contemplated that in other examples, the rotating polygon mirror 110 and the galvanometer 114 can scan the first and second light beams in a scan pattern that is independent in both the x-axis and y-axis. Furthermore, additional scan patterns such as diagonal, circular, rosette, and the like are also contemplated.

Optimally, the first and second light beams are co-aligned as they are directed in the common path 126 from the optical beam combiner/splitter 116 to the patient eye 124 so that they are directed to the same points on the patient eye 124. However, various factors may cause correlation errors in the first and second light beams before they reach the patient eye 124.

Figure 3:
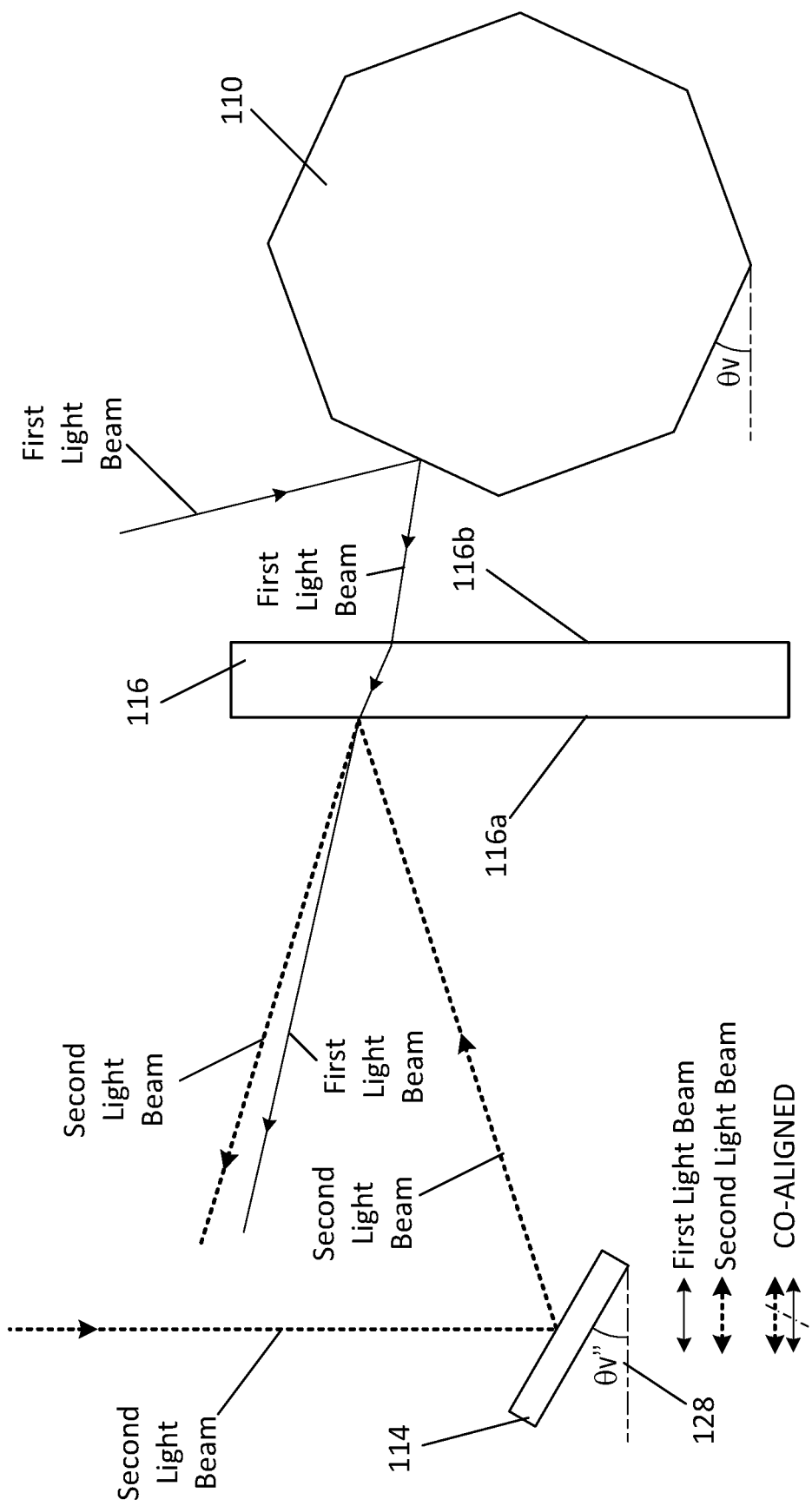
FIG. 3 is a schematic detailed view of an optical beam combiner/splitter in relation to a rotating polygon mirror and a galvanometer scanner of the ophthalmic scanning system.

FIG. 3 is a schematic detailed view of the optical beam combiner/splitter 116 in relation to the rotating polygon mirror 110 and the galvanometer 114. In the example illustrated in FIG. 3, the optical beam combiner/splitter 116 combines the first and second light beams that originated from the first and second light beam imagers 102, 104, respectively. The second light beam, after being directed to the optical beam combiner/splitter 116 by the galvanometer 114, is reflected from a first surface 116a of the optical beam combiner/splitter 116, and the first light beam, after being directed to the optical beam combiner/splitter 116 by the rotating polygon mirror 110, passes through the optical beam combiner/splitter 116 at a second surface 116b and exits at the first surface 116a.

For a given angle θv of the galvanometer 114 or the rotating polygon mirror 110 relative to the optical beam combiner/splitter 116, the second light beam is optimally reflected from the first surface 116a at a same angle as that in which the first light beam exits the first surface 116a such that the first and second light beams are co-aligned. Co-alignment means that the first and second light beams are directed to the same area on the patient eye 124. However, in some instances such as the one shown in FIG. 3, a diffraction error can cause the first and second light beams to have different external angles when they reach the patient eye 124 (see FIG. 2).

Figure 4:
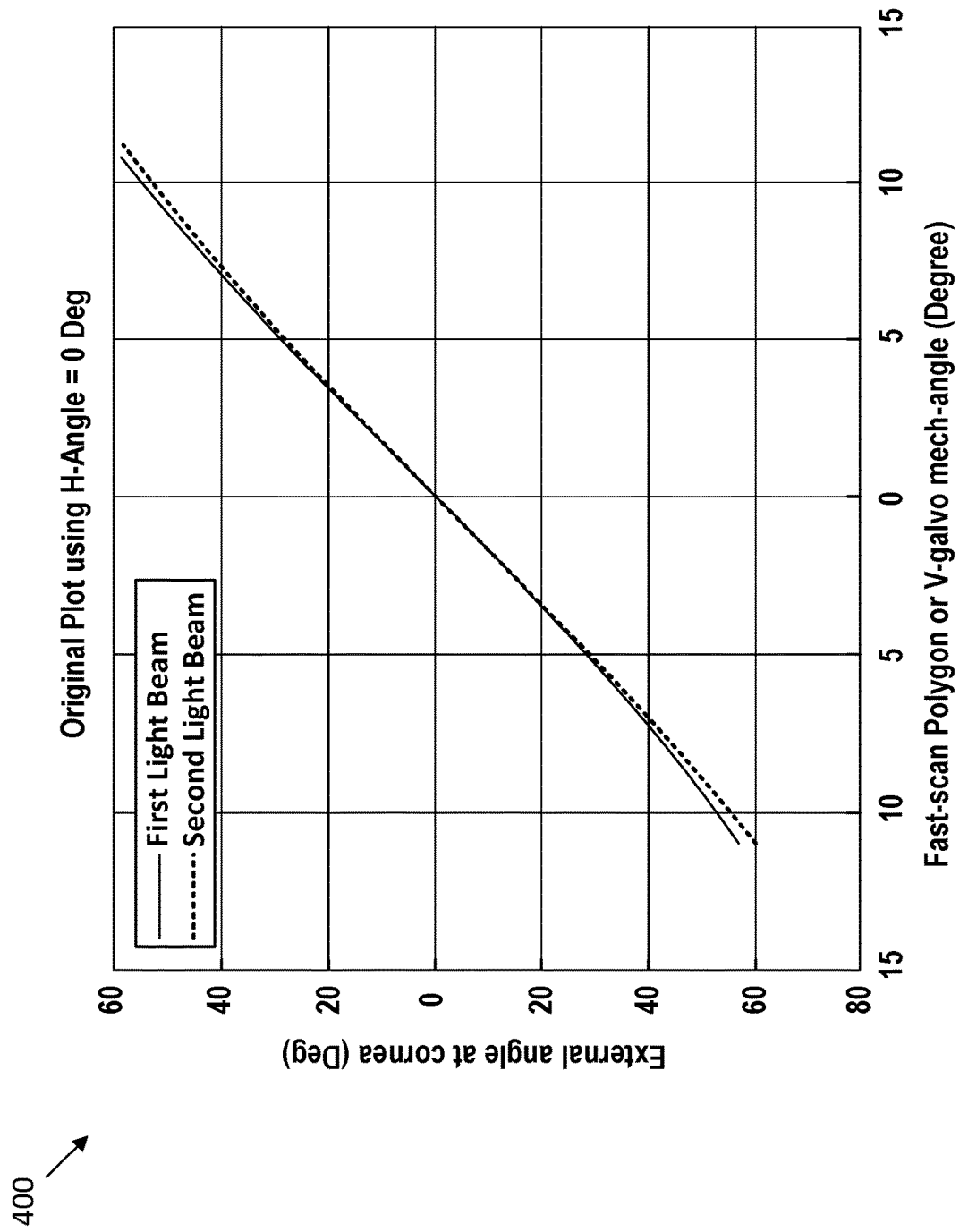
FIG. 4 is a graph that illustrates the effect of a diffraction error on an external angle of a first light beam compared to an external angle of a second light beam.

FIG. 4 depicts a graphic 400 that illustrates the effect of the diffraction error on the first light beam compared to the second light beam as the angle θv of the rotating polygon mirror 110 or galvanometer 114 varies. The diffraction error causes the external angle of the first light beam (i.e., the angle of the light beam going into the patient's eye) to differ from the external angle of the second light beam, at particular angles θv. The difference between the external angles of the first and second light beams increases as the angle θv of the rotating polygon mirror 110 increases or decreases away from 0 degrees such that the error is more pronounced as the field of view of the first and second light beams increases. As described above, in some examples the first light beams are used for an SLO imaging modality while the second light beams are used for an OCT imaging modality.

Figure 5:
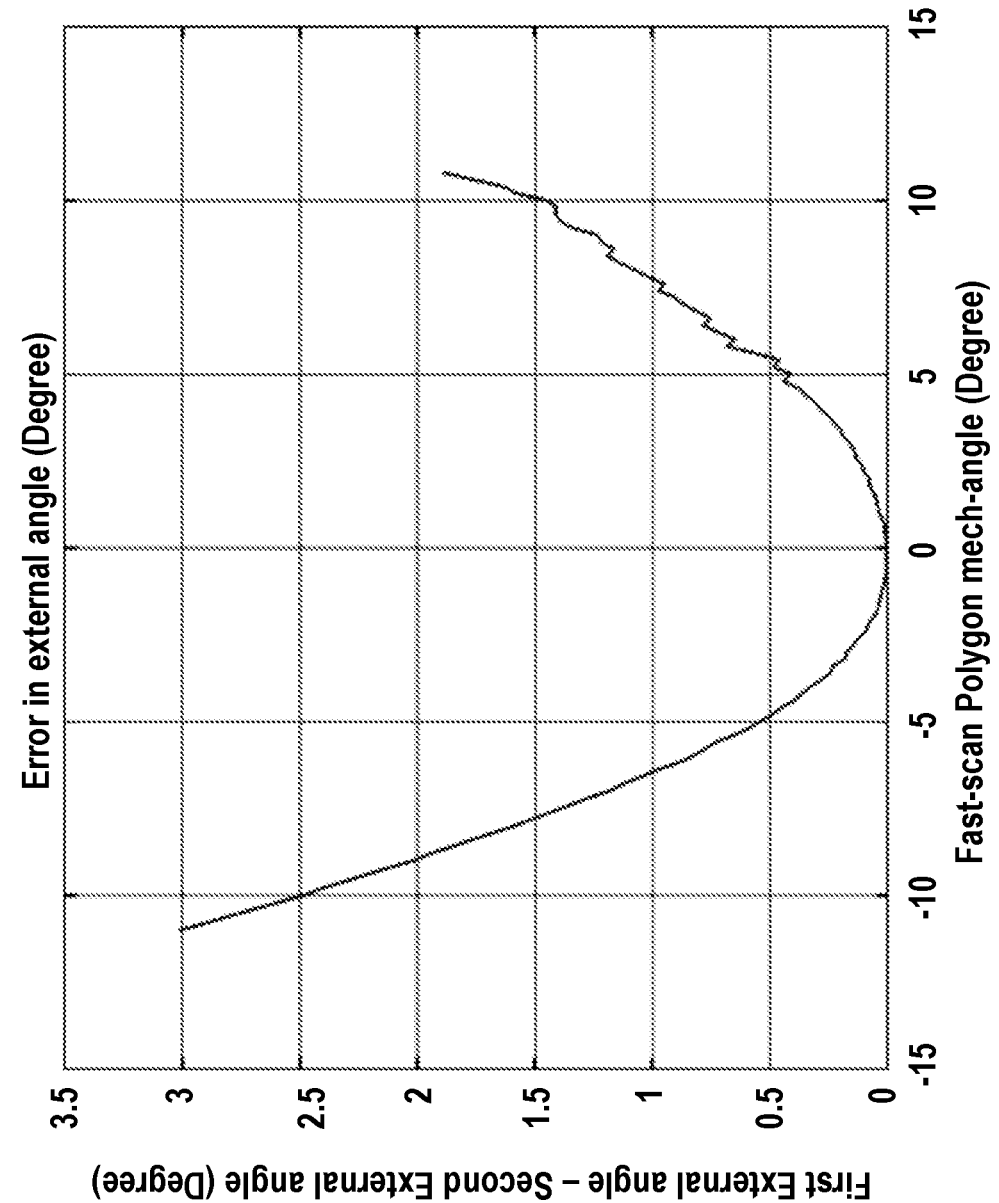
FIG. 5 is a graph that illustrates the error in the external angle of a first light beam as the angle of the rotating polygon mirror varies.

FIG. 5 depicts a graph 500 that illustrates the error in the external angle of the first light beam compared to the external angle of the second light beam as the angle θv of the rotating polygon mirror 110 varies. As shown in FIG. 5, the error in the external angle of the first light beam compared to the external angle of the second light beam increases as the angle θv of the rotating polygon mirror 110 increases or decreases away from 0 degrees. Thus, the error in the first light beam increases as the field of view of the first light beam increases.

In addition to errors from the optical elements in the path of the first and second light beams (e.g., the diffraction error caused by the optical beam combiner/splitter 116), errors may also result from non-linear behavior differences between the first and second light beams. For example, the ratio between the mechanical angle at the optical beam combiner/splitter 116 and the external angle of the light beam that enters the patient's eye can be different for the first and second light beams.

Additionally, non-linear behavior of the external angle of the first and second light beams may result in a transverse (x or y direction) sweep resolution of the light beams to vary as the first and second light beams scan across the eye from top to bottom. This can result in there being non-uniform pixel dimensions that are difficult to correct with image processing. Thus, pixel size to actual physical size encoding preferably should be accounted for to preserve feature size accuracy or linearity between the first and second light beams.

Additional errors may result from the electro-mechanical nature of positioning elements within the ophthalmic scanning system 100. For example, electro-mechanical errors may result from position sensor non-linearity or electrical drive hysteresis which affect the co-alignment of the first and second light beams. The non-linearity of the position sensor may result in errors in pixel dimensions (that may be in addition to non-linear pixel dimensions due to the optical path of the first and second light beams). The effect of these additional errors can be cumulative when used in a closed loop feedback system such as for eye tracking. Non-linear behavior of the galvanometer 114 can increase near the end of sweeps. Further, the electrical drive hysteresis behavior (e.g., for multiple forward and reverse sweeps) may result in significant differences between forward and reverse sweeps.

Figure 6:
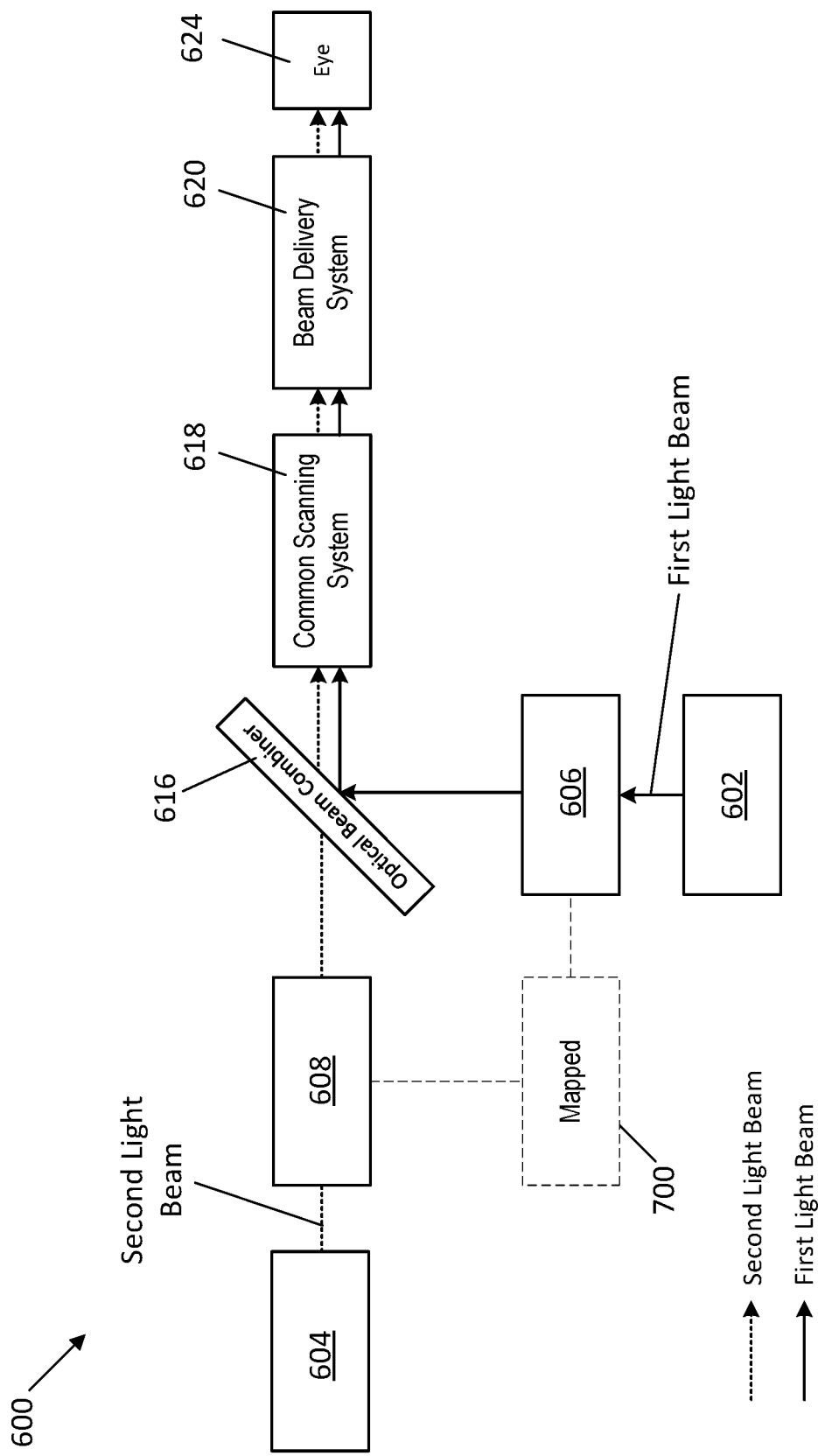
FIG. 6 schematically illustrates an ophthalmic scanning system for mapping a second imaging modality onto a first imaging modality.

FIG. 6 schematically illustrates an ophthalmic scanning system 600 for co-aligning the first light beams and the second light beams, according to an example embodiment herein. The ophthalmic scanning system 600 includes a first light beam imager 602 that transmits a first light beam to a first scanning system 606 that can include, in one example embodiment herein, the rotating polygon mirror 110 described above with reference to FIGS. 2 and 3. In some examples, the first light beam imager 602 is a fundus, SLO, or line imager.

The system 600 includes an second light beam imager 604 that transmits a second light beam to a second scanning system 608 that can include, in one example embodiment herein, the focus mechanism 112 and galvanometer 114 described above with reference to FIGS. 2 and 3. In some examples, the second light beam imager 604 is an OCT or SLO imager.

A control system 700 maps the second light beam onto the first light beam by compensating the galvanometer in the second scanning system 608 to adjust the internal angle of the second light beam directed to the optical beam combiner/splitter 616. The optical beam combiner/splitter 616 is similar to the optical beam combiner/splitter 116 described above. In some examples, the optical beam combiner/splitter 616 is a dichroic mirror that is able to both combine and split the first and second light beams.

The optical beam combiner/splitter 616 combines/co-aligns the first and second light beams and directs the co-aligned first and second light beams to a common scanning system 618. The common scanning system 618 can include the slit mirror 118, secondary galvanometer scanner 120, and main mirror 122 described above with reference to FIG. 2, in one example embodiment herein. Accordingly, in at least some examples, the first and second light beam imagers 602, 604 share part of an optical path.

The optical beam combiner/splitter 116 can also split the first and second light beams reflected back from patient eye 624 (by way of beam delivery system 620 and common scanning system 618) and directs the reflected first and second light beams back to the first and second light beam imagers 102, 104, respectively, for image processing and analysis.

Beam delivery system 620 transmits the co-aligned first and second light beams received from the common scanning system 618 to the patient eye 624. The beam delivery system 620 can include, in one example embodiment herein, one or more lenses (not shown) for delivering the co-aligned first and second light beams, in either direction.

Figure 7:
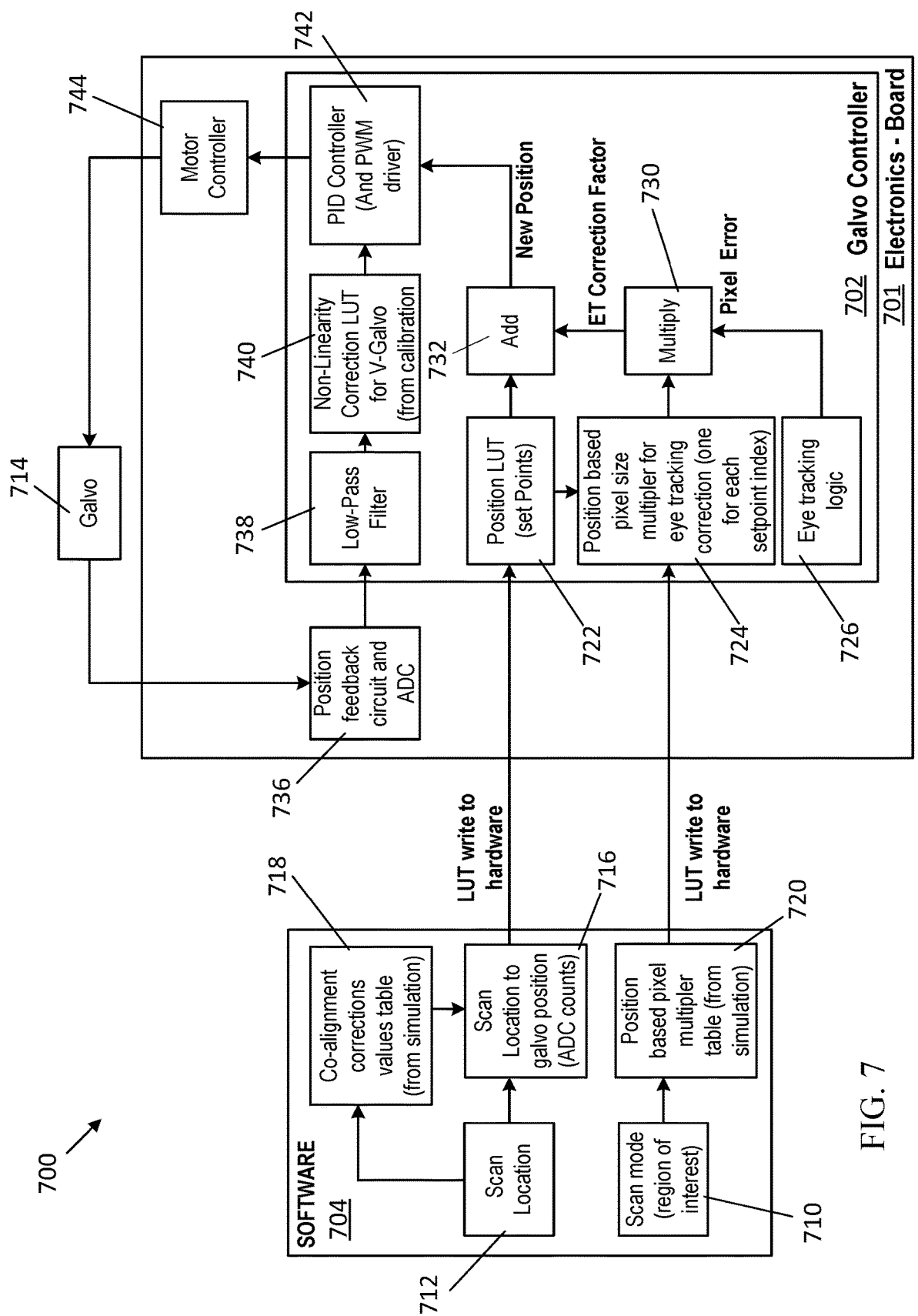
FIG. 7 schematically illustrates an ophthalmic scanning system that has a control system and software component for mapping a second imaging modality onto a first imaging modality.

FIG. 7 schematically illustrates the control system 700 of FIG. 6 in greater detail. The control system 700 uses the first imaging modality as a reference and maps the second imaging modality onto the first imaging modality by compensating for at least one of an optical-mechanical and an electro-mechanical projection difference between the first and second imaging modalities, and thereby aligning all scan system differences and optical path differences between the first and second modalities. The control system 700 corrects errors that may otherwise occur when using multiple modalities that do not share a common optical path.

As described above, in some examples, the first imaging modality is an SLO imaging modality and the second imaging modality is an OCT imaging modality. For each of the first and second modalities, the control system 700 enables the ophthalmic scanning system to scan a same location with repeatability, provides first and second laser light beam co-alignment, and corrects errors from first and second non-linearity and position dependent resolution. The control system 700 enables the ophthalmic scanning system to scan retina pathologies to have the same location, size, shape, and dimensions across the first and second modalities.

The control system 700, in one example embodiment herein, utilizes various look-up tables (LUTs) to control the position and movement of a galvanometer 714 of an imaging modality, and thereby provide improved scan location accuracy and correlation between the first and second imaging modalities: a co-alignment correction look-up table 718 for providing co-alignment correction; a position-based pixel multiplier look-up table 720 for providing target tracking compensation; and a non-linearity corrections look-up table 740 for providing non-linearity and hysteresis correction. The control system 700 uses these look-up tables to map the second imaging modality onto the first imaging modality, while also providing target tracking and non-linearity compensation. In some examples, the data used to generate the look-up tables is derived from at least one of or a combination of the following: systematic data based on modelling; systematic data based on calibration; biometry information; and fixation and patient positioning error with respect to the imaging system access.

The control system 700 includes an electronics board 701, a galvanometer controller 702, and a software module 704 that are used in combination to control the galvanometer 714. In some examples, the galvanometer 714 is similar to the galvanometer 114 described above.

The software module 704 includes a region of interest 710 for the first imaging modality to generate an image. The region of interest 710 is used as a reference for determining a scan location 712 for the second imaging modality. The scan location 712 can be a portion or subset of the region of interest 710 scanned by the first imaging modality such as a location where a feature or pathology is identified within an image generated by the first imaging modality.

In some examples, the scan location 712 for the second imaging modality is the same as the region of interest 710 of the first imaging modality. In other examples, the scan location 712 for the second imaging modality is different from the region of interest 710 of the first imaging modality. In some examples, a scan field of view for the second imaging modality is the same as a scan field of view for the first imaging modality. In further examples, a scan field of view for the second imaging modality is different from a scan field of view for the first imaging modality.

The scan location 712 is converted into a galvanometer position 716. The galvanometer position 716 is based on analog-to-digital converter (ADC) values to control the position of the galvanometer 714. The galvanometer position 716 is adjusted by the co-alignment correction look-up table 718 to compensate for scan location and alignment errors described above.

The co-alignment correction look-up table 718 provides an internal angle to external angle correction for the galvanometer position 716. The co-alignment correction look-up table 718 uses data acquired from simulation models that estimate errors in the external angle of the first light beam of the first imaging modality relative to a second light beam of the second imaging modality (e.g., see FIG. 5) to determine mechanical angle correction for the galvanometer 714. Thus, the co-alignment correction look-up table 718 is used to compensate the galvanometer position 716 to reduce and/or eliminate the error between the external angles of the first and second light beams of the first and second imaging modalities.

Figure 8:
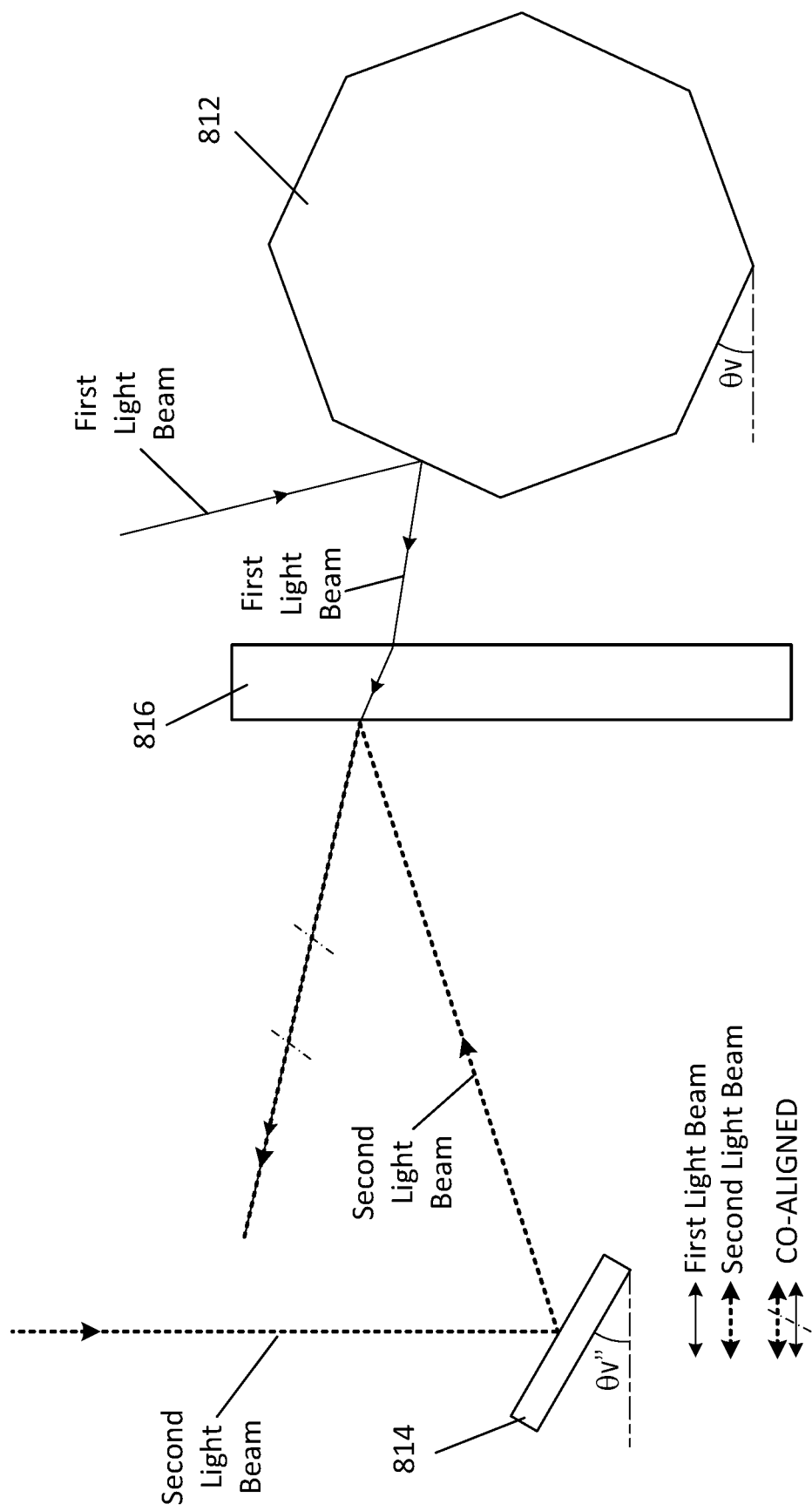
FIG. 8 is a schematic detailed view of an optical beam combiner/splitter in relation to a rotating polygon mirror and a compensated galvanometer scanner.

FIG. 8 is a schematic detailed view of an optical beam combiner/splitter 816 in relation to a rotating polygon mirror 812 used for directing the first light beam of the first imaging modality and a galvanometer 814 used for directing the second light beam of the second imaging modality. The galvanometer 814 is compensated by the co-alignment correction look-up table 718 to eliminate errors between the external angles of the first and second light beams. Thus, the galvanometer 814 is positioned by the control system 700 to adjust the angle of the second light beam directed to the optical beam combiner/splitter 816 such that the external angle of the second light beam is mapped onto the external first light beam to co-align the first and second light beams of the first and second imaging modalities.

Figure 9:
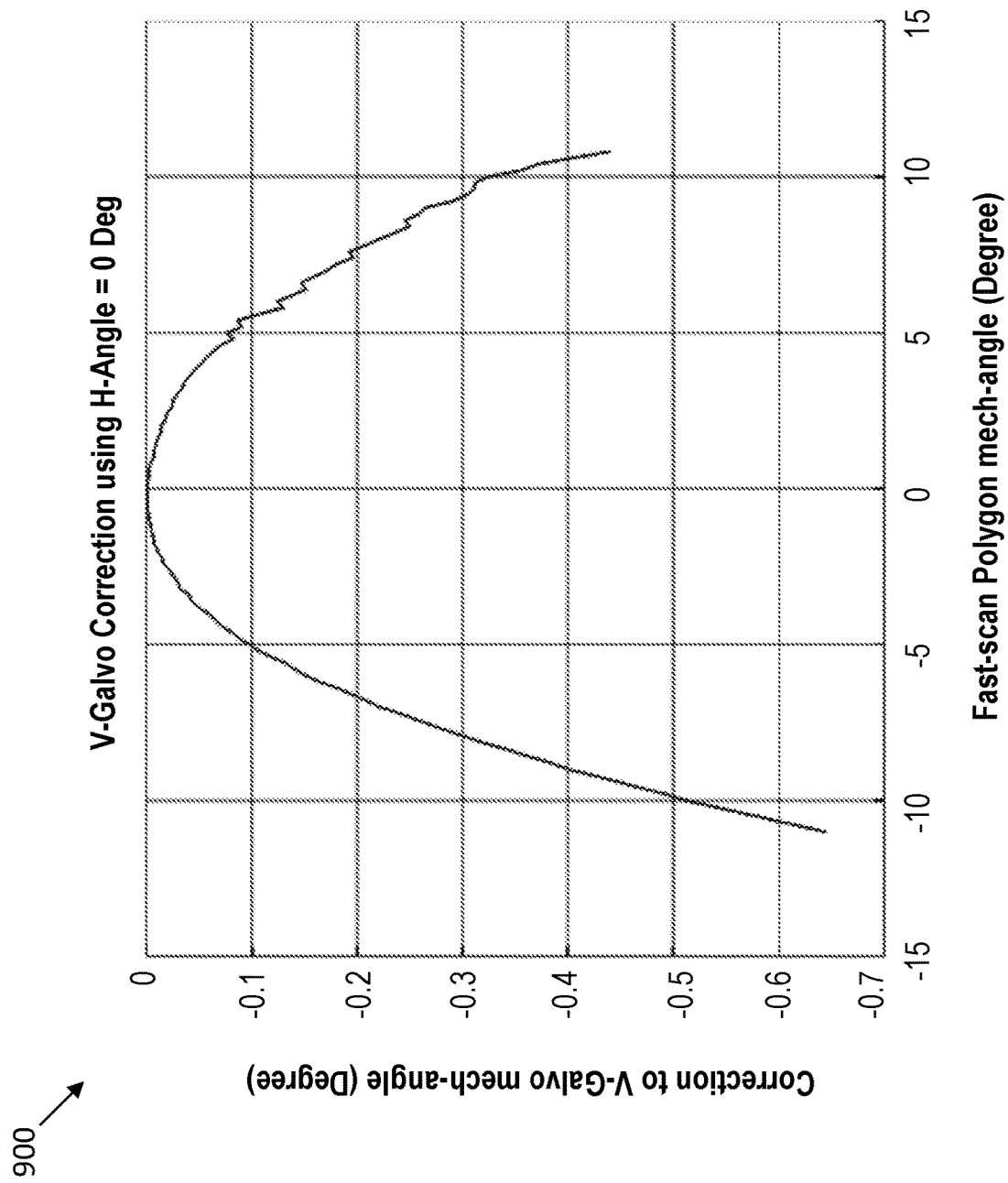
FIG. 9 is a graph that illustrates the mechanical angle correction of a galvanometer scanner used for mapping a second light beam onto a first light beam.

FIG. 9 depicts a graph 900 that illustrates mechanical angle correction data that is included in the co-alignment correction look-up table 718 for adjusting the angle θv of the galvanometer 814 (see FIG. 8) to map the second light beam onto the first light beam. As shown in FIG. 9, the mechanical angle correction of the galvanometer 814 increases as the angle θv of the rotating polygon mirror 812 increases or decreases away from 0 degrees (i.e., in the left or right directions of the x-axis). Thus, the mechanical angle correction of the galvanometer 814 increases as the field of view of the first and second light beams increases.

Referring back to FIG. 7, in some scenarios, co-alignment correction look-up table 718 is not utilized to compensate the galvanometer position 716 (see arrow linking the scan location 712 directly to the galvanometer position 716). This may occur when the ophthalmic scanning system performs only the second scan modality without performing the first scan modality.

Also shown in FIG. 7, the position-based pixel multiplier look-up table 720 is used to compensate for non-uniform pixel dimensions of the first and second light beams as the light beams scan across the patient's eye. Further, the position-based pixel multiplier look-up table 720 is used to convert output from an eye tracking logic 726 (described in more detail below) into ADC values depending on real-time scan position.

Figures 10, 11:
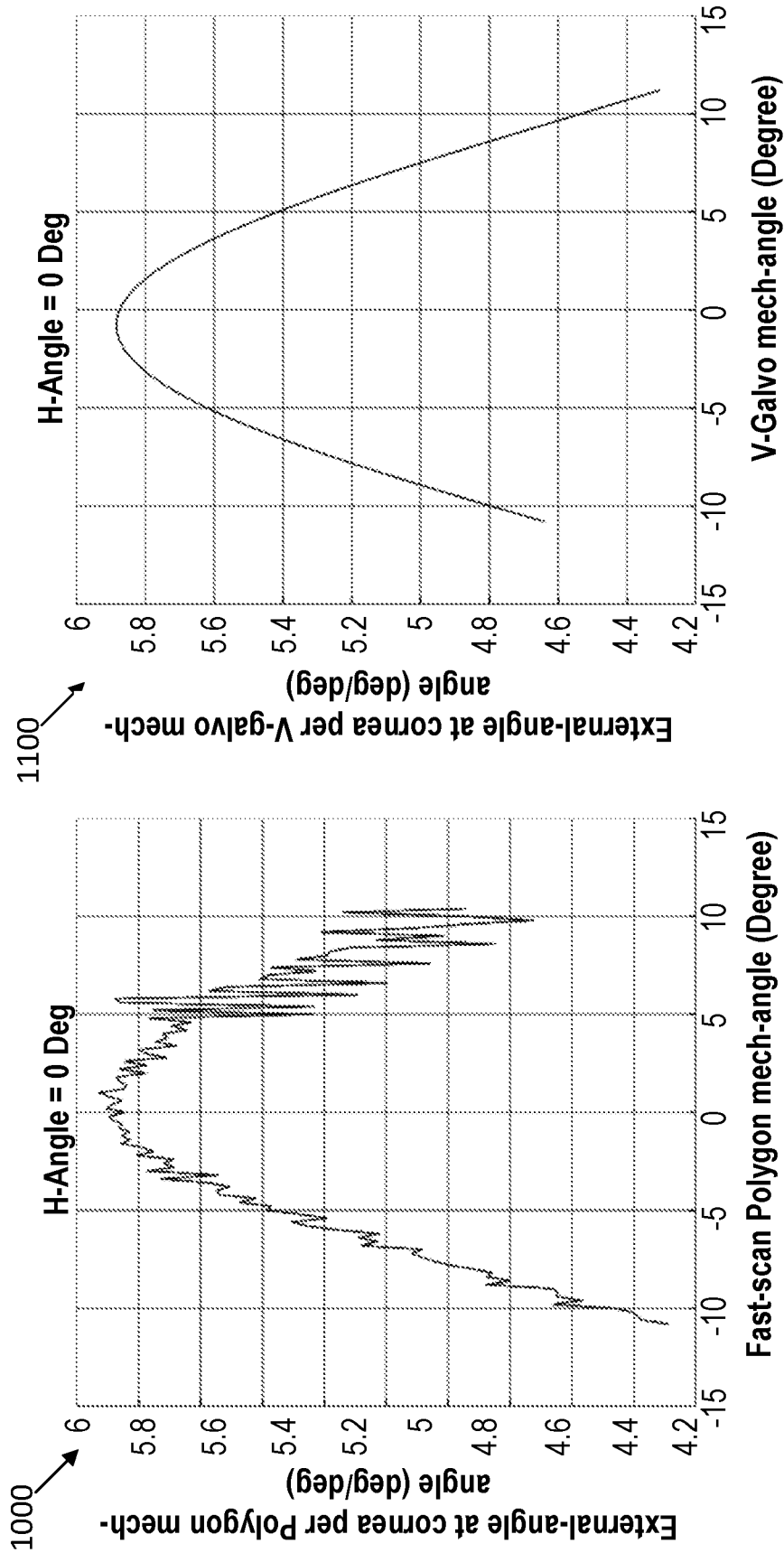
FIG. 10 is a graph that illustrates scaling factors to compensate for non-uniform pixel dimensions from a rotating polygon mirror of a first imaging modality.
FIG. 11 is a graph that illustrates scaling factors to compensate for non-uniform pixel dimensions from a galvanometer scanner of a second imaging modality.

Different scaling factors from the position-based pixel multiplier look-up table 720 are used for compensating the first and second light beams for each mechanical angle of the respective rotating polygon mirror 812 and galvanometer 814 (see FIG. 8). The position-based pixel multiplier look-up table 720 uses data acquired from simulation models. For example, FIG. 10 depicts a graph 1000 (that may be used by the position-based pixel multiplier look-up table 720) that displays scaling factors (e.g., y-axis) for compensating for non-uniform pixel dimensions caused by the rotating polygon mirror 812. FIG. 11 depicts a graph 1100 (that may be used by the position-based pixel multiplier look-up table 720) that displays scaling factors (e.g., y-axis) for compensating for the non-uniform pixel dimensions from the galvanometer 814.

In some example scenarios, the position-based pixel multiplier look-up table 720 is not utilized to compensate the galvanometer position 716. For example, the position-based pixel multiplier look-up table 720 is not used when the system does not have a non-linear scan location dependent pixel to ADC value relation. In these examples, the ADC values for the galvanometer position 716 are transmitted directly from that element of software module 704 to the galvanometer drive position look-up table 722 in the galvanometer controller 702.

The galvanometer drive position look-up table 722 is a memory of the galvanometer controller 702 that stores the ADC values from the galvanometer position 716 to control the position of the galvanometer 714. The inputs in the galvanometer drive position look-up table 722 thus control the location where it is desired for the galvanometer 714 to move and start scanning. The inputs can be stored in a plurality of different waveforms in the galvanometer drive position look-up table 722. Advantageously, combining the drive and co-alignment correction values in the same memory leads to a reduction in real-time storage for the galvanometer controller 702.

When the galvanometer drive position look-up table 722 obtains the ADC values from the galvanometer position 716, the ADC values are thereafter compensated by a position-based pixel multiplier 724 in the galvanometer controller 702. The position-based pixel multiplier 724 is a memory of the galvanometer controller 702. In the some examples, the position-based pixel multiplier 724 stores only a portion or subset of the position-based pixel multiplier look-up table 720 to save memory in the galvanometer controller 702.

The galvanometer controller 702 includes an eye tracking logic 726 that generates an adjustment of the scan pattern to compensate for eye and/or head movements of the patient. The position-based pixel multiplier 724 is used to convert outputs from the eye tracking logic 726 that are in pixels into ADC values for use by the galvanometer drive position look-up table 722. In some examples, the adjustment is non-linear such that a multiplier 730 is used to compensate the ADC values from the position-based pixel multiplier 724 for the different pixel scaling in the different regions of the patient's eye. The multiplier 730 converts the ADC values in accordance with the pixel scaling for the different regions of the eye to adjust the position for the galvanometer 714 based on the eye tracking logic 726.

The output from the position-based pixel multiplier 724 is used to convert eye tracking pixel errors from the eye tracking logic 726 into galvanometer drive values by multiplication. The multiplier 730 is not a constant, in one example embodiment herein. Instead, by example, the multiplier 730 is scan position dependent. Thus, the scan position is obtained from the galvanometer drive position look-up table 722, and a multiplier is selected from the position-based pixel multiplier 724, and the eye tracking pixel error is multiplied by the multiplier 730 to provide a galvanometer drive error summed into the drive waveform at memory block 732. Thus, memory block 732 combines the scan position from the galvanometer drive position look-up table 722 with an offset from the eye tracking logic 726 via the multiplier 730 after multiplication with non-linear pixel correction coefficients from the position-based pixel multiplier 724. The drive waveform is then fed into a PID controller and PWM driver 742 that drives a motor controller 744 for directing the position and movement of the galvanometer 714.

In one illustrative example, the eye tracking logic 726 receives an SLO image while OCT scanning is taking place. The eye tracking logic 726 compares the incoming SLO image with a reference image. In some examples, the reference image is derived from an image early in the scan sequence or from a reference SLO planning image. The output of eye tracking logic 726 is in pixels (x-axis and y-axis coordinates), which the SLO image is offset with respect to the reference image. These pixel errors are multiplied by the multiplier 730 to convert them to galvanometer drive values (i.e., ADC values). The conversion is non-linear, and is scan position dependent, in one example embodiment herein. Thus, the position-based pixel multiplier 724 provides the correct multiplier for the current scan location (in ADC values).

Still referring to FIG. 7, a non-linearity corrections look-up table 740 also can be used to adjust the position of the galvanometer 714 to compensate for non-linearity of the first and second light beams and hysteresis effects on the galvanometer 714, as will be described below. First, FIGS. 12 and 13 will be described.

Figure 12:
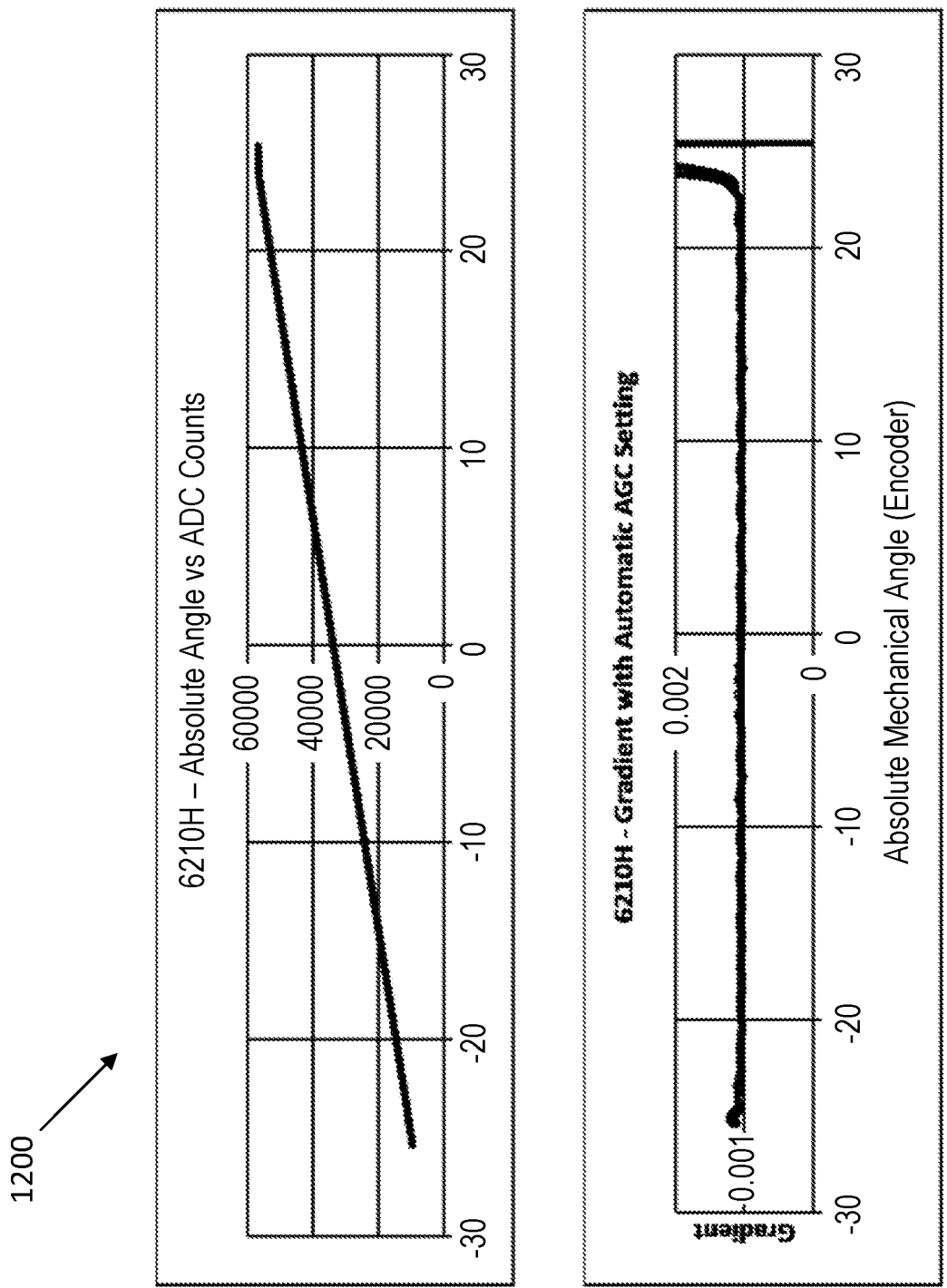
FIG. 12 is a graph that illustrates a gradient of ADC values over the mechanical angles of a galvanometer that provides forward and reverse sweeps.

FIG. 12 depicts a graph 1200 displaying ADC values over the mechanical angle of the galvanometer 714 (top curve) and a gradient of the ADC values over the mechanical angle of the galvanometer 714 (bottom curve). As shown in FIG. 12, the ADC values roll-off at the ends of the movement (i.e., sweeps) of the galvanometer 714. Thus, the relationship between the ADC values and the galvanometer position changes depending on the position of galvanometer such that the relationship is non-linear at opposite ends of the field of view of the galvanometer 714 (e.g., the ends of the sweeps). The non-linearity of the ADC values exists from how the galvanometer 714 is driven when reflecting the second light beams or from the position sensors of the galvanometer 714 which produce analog output signals that identify the position of the galvanometer). The effect of the non-linearity (when left uncompensated) is that the galvanometer will not be correctly pointed to the desired position at all scan angles. Instead, the galvanometer will incorrectly report the "correct position" and the control system 700 will be unable to detect that the galvanometer is incorrectly pointed in the wrong direction.

Figure 13:
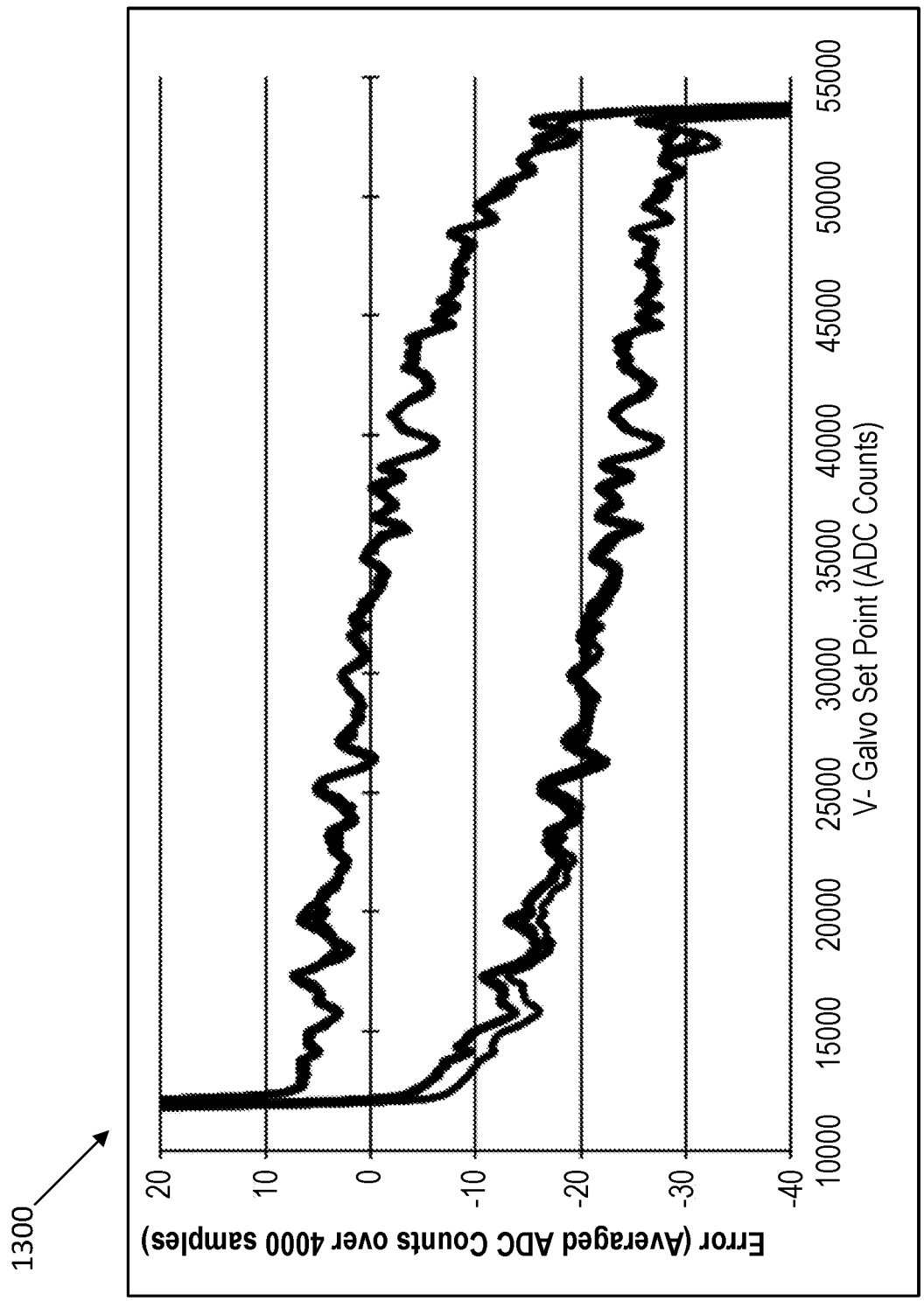
FIG. 13 is a graph that illustrates the electrical drive hysteresis that results from the forward and reverse sweeps of a galvanometer.

FIG. 13 depicts a graph 1300 that illustrates an electrical drive hysteresis from forward and reverse sweeps of the galvanometer 714. The hysteresis from reversed wave forms causes the same ADC values to have different mechanical angles at each location of the galvanometer 714 for the entire sweep range from end to end. (In one illustrative, non-limiting example, hysteresis may occur where the positon of galvanometer 714 is driven to a position 30,000, and where an angle of the galvanometer 714 is pointing to either −20 or 0 degrees, depending on movement +ve or −ve. Also in one illustrative, non-limiting example, such an error can be compensated locally in software for a scan angle by over-driving the galvanometer using parameters such as, e.g., gain and dc-offset, which eventually results in a location for both forward and reverse sweeps that is close to an originally planned location).

Referring back to FIG. 7, the non-linearity corrections look-up table 740 receives inputs from a low-pass filter 738, which receives inputs from a position feedback circuit 736. The non-linearity corrections look-up table 740 stores data acquired from simulation models (such as the data included in graphs 1200 and 1300), wherein the stored data is used to compensate for non-linearity of ADC values and hysteresis of the galvanometer 714. Based on position information of galvanometer 714 received from the position feedback circuit 736 by way of the low-pass filter 738, the non-linearity corrections look-up table 740 is used to provide compensated position information to the PID controller and PWM driver 742.

The PID controller and PWM driver 742 responds to the compensated position information, received from the non-linearity corrections look-up table 740, by controlling a motor controller 744 to control the position and movement of the galvanometer 714 based on the new position information. The PID controller and PWM driver 742 uses the error between the current position of the galvanometer 714 (output of 740) and the desired position of the galvanometer 714 (output from memory block 732) to drive the galvanometer 714 to the correct position. In some examples, the non-linearity corrections look-up table 740 corrects for position sensor errors from the galvanometer 714. The output from the memory block 732 corrects the drive position errors (i.e., from eye tracking or known optical errors in the system), so that the output of memory block 732 is the desired drive value for the galvanometer 714. The galvanometer 714 then performs a scan over a target area. In some examples the galvanometer 714 performs an optical coherence tomography (OCT) scan over the target area.

When the location and movement of the galvanometer 714 is controlled in accordance with the control system 700, the ratio of the mechanical angle to the external angle for second light beam path of the second imaging modality becomes the same as the ratio of the mechanical angle to the external angle for first light beam path of the first imaging modality. Thus, the control system 700 provides improved scan location accuracy and correlation between the first and second imaging modalities and enables the first and second imaging modalities to have a wider field view in an ophthalmic scanning system. For example, the first and second imaging modalities can have a 200 degree field of view that includes about 80 percent of the retina while significantly reducing scan location errors, scan sizing errors, and scan linearity errors.

Advantageously, the control system 700 enables an ophthalmic scanning system to cover a wider scanning range (i.e., an ultra-wide-field) while providing improved scan linearity and accuracy throughout the entire scanning range. Additionally, errors between the first and second imaging modalities are made negligible at the scanner level to achieve a high level of scan resolution and repeatability such that post-imaging processing is not needed to correct for the scan location and resolution differences between the first and second imaging modalities. Furthermore, the control system 700 can substantially reduce the effects of hysteresis and non-linearity on the galvanometer 714.

Figure 14:
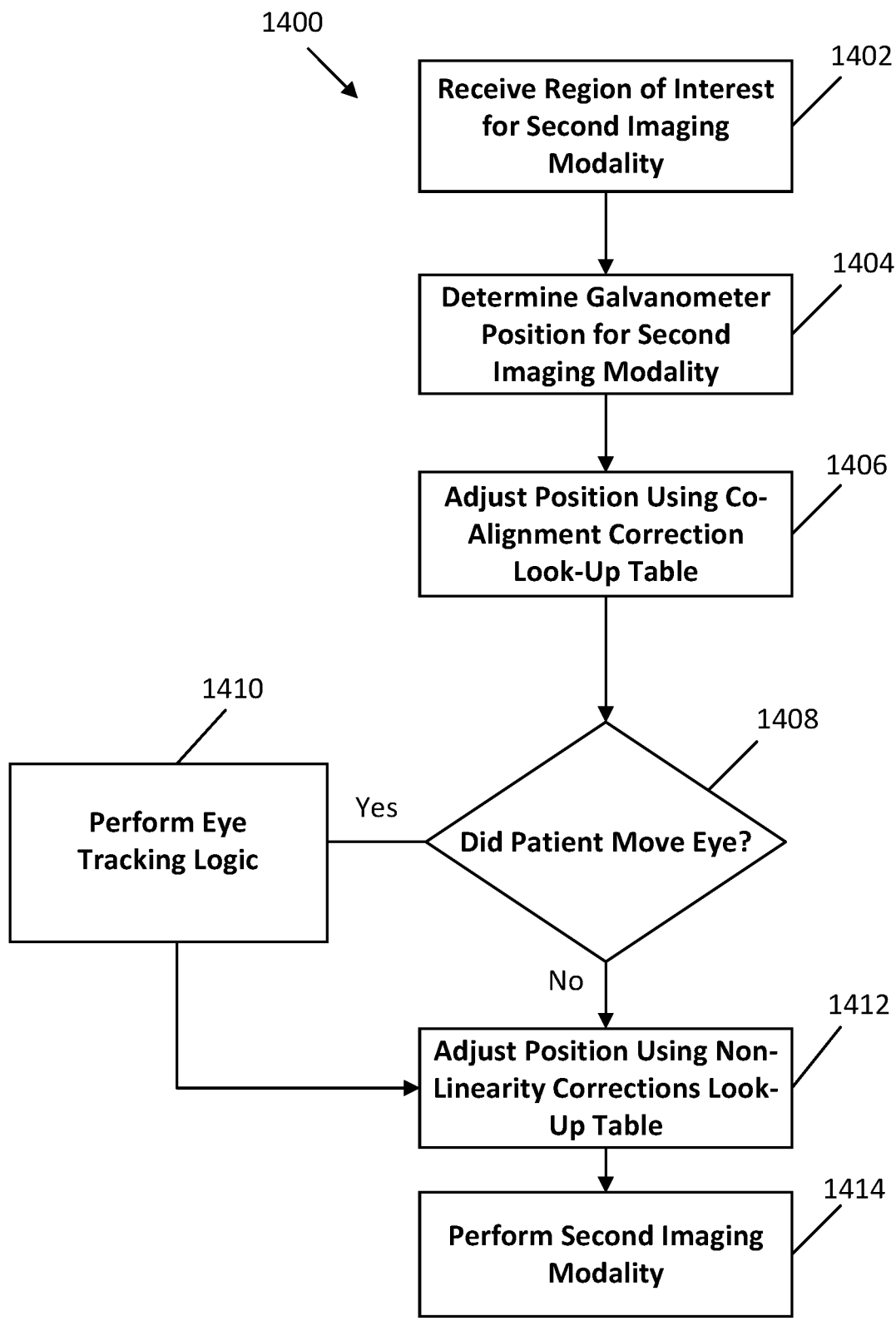
FIG. 14 illustrates an example method of mapping a second imaging modality onto a first imaging modality.

FIG. 14 illustrates a method 1400 of mapping a second imaging modality onto a first imaging modality, according to an example embodiment herein. As described above, in some examples the first imaging modality is an SLO imaging modality and the second imaging modality is an OCT imaging modality. The method 1400 includes an operation 1402 of receiving a scan location for the second imaging modality (e.g., the scan location 712 of FIG. 7) based on a region of interest imaged by the first imaging modality (e.g., the region of interest 710 of FIG. 7). The scan location can be a feature or pathology identified within the region of interest imaged by the first imaging modality. The method 1400 then determines at operation 1404 an initial galvanometer position for the second imaging modality (e.g., the galvanometer position 716 of FIG. 7) based on the scan location received from operation 1402.

Next, the method 1400 includes an operation 1406 of adjusting the initial galvanometer position for the second imaging modality using a co-alignment correction look-up table (e.g., the co-alignment correction look-up table 718 of FIG. 7). As described above, the co-alignment correction look-up table provides an internal angle to external angle correction for the galvanometer position to adjust the galvanometer position to compensate for the errors between the external angles of the first and second light beams at the target area.

Next, the method 1400 at operation 1408 determines whether the target area has moved (e.g., when the patient moves their eye). If it is determined that the target area has moved (i.e., "yes" in operation 1408), the method 1400 proceeds to operation 1410 to perform an eye tracking logic that generates an adjustment of the scan pattern to compensate for eye and/or head movements of the patient. As described above, a look-up table such as the position-based pixel multiplier 724 can be used to convert outputs from the eye tracking logic that are in pixels into ADC values to adjust the galvanometer position. Different scaling factors are provided in the look-up table for compensating for the non-uniform pixel dimensions.

If it is determined that the target area has not moved (i.e., "no" in operation 1408) or after completion of performing the eye tracking logic in operation 1410, the method 1400 proceeds to operation 1412 where a non-linearity corrections look-up table (e.g., the non-linearity corrections look-up table 740 of FIG. 7) is used to adjust the position of the galvanometer to compensate for the non-linearity and the hysteresis effects on the galvanometer. Thereafter, the method 1400 proceeds to operation 1414 by performing a scan of the target area by the second imaging modality. In some examples, the scan performed at operation 1414 is an OCT scan.

Figure 15:
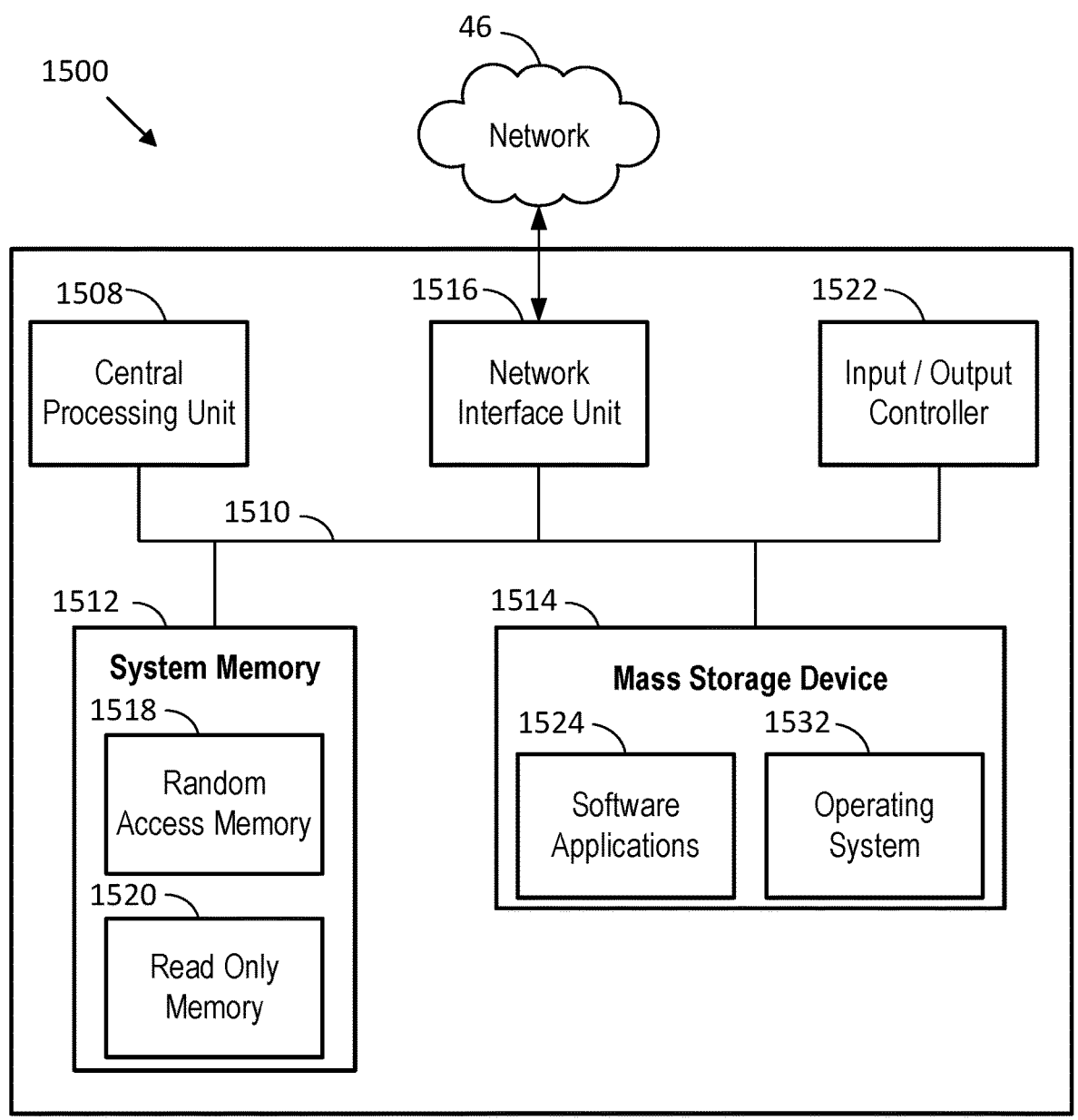
FIG. 15 illustrates example physical components of a computing device.

FIG. 15 illustrates example physical components of a computing device 1500, such as the computing device or devices associated with the ophthalmic scanning systems described above. As shown, the computing device 1500 includes at least one processor or central processing unit ("CPU") 1508, a system memory 1512, and a system bus 1510 that couples the system memory 1512 to the CPU 1508. The central processing unit 1508 is an example of a processing device.

The system memory 1512 includes a random access memory ("RAM") 1518 and a read-only memory ("ROM") 1520. A basic input/output system containing the basic routines that help to transfer information between elements within the computing device, such as during startup, is stored in the ROM 1520. The computing device further includes a mass storage device 1514. The mass storage device 1514 is able to store software instructions and data. The mass storage device 1514 is connected to the CPU 1508 through a mass storage controller connected to the system bus 1510. The mass storage device 1514 and its associated computer-readable data storage media provide non-volatile, non-transitory storage for the computing device 1500. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions. The mass storage device 1514 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device.

The computing device 1500 may operate in a networked environment using logical connections to remote network devices through the network 46, such as a local network, the Internet, or another type of network. The computing device 1500 connects to the network 46 through a network interface unit 1516 connected to the system bus 1510. The network interface unit 1516 may also connect to other types of networks and remote computing systems.

The computing device 1500 includes an input/output controller 1522 for receiving and processing input from a number of other devices, including a touch user interface display screen, or another type of input device. Similarly, the input/output controller 1522 may provide output to a touch user interface display screen, a printer, or other type of output device.

As mentioned above, the mass storage device 1514 and the RAM 1518 of the computing device 1500 can store software instructions and data. The software instructions include an operating system 1532 suitable for controlling the operation of the computing device 1500. The mass storage device 1514 and/or the RAM 1518 also store software instructions, that when executed by the CPU 1508, cause the computing device 1500 to provide the functionality discussed in this document, including the methods described herein and shown in the Figures.

Communication media may be embodied in the software instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, communication media may include wired media such as a wired network or direct-wired connection, and wireless media such as acoustic, radio frequency (RF), infrared, and other wireless media.

The block diagrams depicted herein are just examples. There may be many variations to these diagrams described therein without departing from the spirit of the disclosure. For instance, components may be added, deleted or modified.

In the foregoing description, example aspects are described with reference to several example embodiments. Accordingly, the specification is illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment (and can form a memory or store). The program or instructions on the non-transitory machine-accessible medium, machine-readable medium, memory, instruction store, or computer-readable storage device or medium, may be used to program a computer system or other electronic device. The machine- or computer-readable device/medium, memory, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable medium", "machine-accessible medium", "machine-readable medium", "memory", "instruction store", "computer-readable storage medium", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, memory, instruction store(s), or storage device(s), having instructions stored thereon or therein which can be used to control, or cause, a computer or computer processor to perform any of the procedures of the example embodiments described herein. The storage medium/memory/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, memory, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The devices and apparatus described herein may be embodied in other specific forms without departing from the characteristics thereof. The foregoing embodiments are illustrative rather than limiting of the described systems and methods. Scope of the optical systems and apparatuses described herein is thus indicated by the appended claims, rather than the foregoing description, and changes that come within the meaning and range of equivalence of the claims are embraced therein.

What is claimed is:

1. An ophthalmic scanning system comprising:
   a first imaging modality;
   a second imaging modality different from the first imaging modality; and
   a control system that maps the first imaging modality to the second imaging modality by compensating for at least one of an optical-mechanical and an electro-mechanical projection difference between the first and second imaging modalities, providing a scan location for the second imaging modality based on a scan location of the first imaging modality.

2. The ophthalmic scanning system of claim 1, wherein the first and second imaging modalities share part of an optical path.

3. The ophthalmic scanning system of claim 1, wherein the first imaging modality is a fundus, SLO, or line imager.

4. The ophthalmic scanning system of claim 1, wherein the second imaging modality is an OCT or SLO imager.

5. The ophthalmic scanning system of claim 1, wherein the scan location for the first and second imaging modalities is the same or different.

6. The ophthalmic scanning system of claim 1, wherein a scan field of view for the first and second imaging modalities is the same or different.

7. The ophthalmic scanning system of claim 1, wherein the control system maps the first imaging modality to the second imaging modality by using a co-alignment correction look-up table that includes data acquired from simulation models that estimate errors in an external angle of the first imaging modality relative to an external angle of the second imaging modality at the scan location for the second imaging modality.

8. The ophthalmic scanning system of claim 1, wherein the control system controls the position of a galvanometer to adjust an internal angle of the second imaging modality such that an external angle of the second imaging modality is mapped onto an external angle of the first imaging modality.

9. The ophthalmic scanning system of claim 1, wherein the control system utilizes a position-based pixel multiplier look-up table to compensate for non-uniform pixel dimensions of the first and second imaging modalities.

10. The ophthalmic scanning system of claim 9, wherein different scaling factors are used for compensating the non-uniform pixel dimensions of the first and second imaging modalities, respectively.

11. The ophthalmic scanning system of claim 9, wherein the position-based pixel multiplier look-up table uses data acquired from simulation models.

12. The ophthalmic scanning system of claim 1, wherein the control system utilizes a non-linearity corrections look-up table to adjust the position of a galvanometer of the second imaging modality to compensate for non-linearity of the second imaging modality and hysteresis of the galvanometer.

13. The ophthalmic scanning system of claim 1, wherein the first and second imaging modalities scan in a pattern that shares at least one common axis.

14. The ophthalmic scanning system of claim 1, wherein the first imaging modality includes a rotating polygon mirror that scans a first light beam to have a vertical pattern in the scan location for the first imaging modality, and the second imaging modality includes a galvanometer that scans a second light beam in the same vertical pattern.

15. The ophthalmic scanning system of claim 1, wherein the first imaging modality includes a rotating polygon mirror that scans a first light beam to have a horizontal pattern in the scan location for the first imaging modality, and the second imaging modality includes a galvanometer that scans a second light beam in the same horizontal pattern.

16. The ophthalmic scanning system of claim 1, wherein the first and second scanning systems do not share a common optical path.

17. A method of mapping first and second imaging modalities, the method comprising:
   receiving a scan location for the first imaging modality; and
   providing a scan location for the second imaging modality based on the scan location of the first imaging modality by compensating for at least one of an optical-mechanical and an electro-mechanical projection difference between the first and second imaging modalities.

18. The method of claim 17, further comprising: adjusting a galvanometer position of the second imaging modality using a position-based pixel multiplier look-up table to compensate for non-uniform pixel dimensions of the second imaging modality.

19. The method of claim 17, further comprising: performing eye tracking logic to adjust a galvanometer position of the second imaging modality.

20. The method of claim 17, further comprising: using a non-linearity corrections look-up table to adjust a galvanometer position of the second imaging modality to compensate for non-linearity of the second imaging modality and hysteresis.

* * * * *